US006985557B2

(12) United States Patent  (10) Patent No.: US 6,985,557 B2
Jaafar  (45) Date of Patent: Jan. 10, 2006

(54) X-RAY APPARATUS WITH FIELD EMISSION CURRENT STABILIZATION AND METHOD OF PROVIDING X-RAY RADIATION THERAPY

(75) Inventor: Ali Jaafar, Eden Prairie, MN (US)

(73) Assignee: Minnesota Medical Physics LLC, Edina, MN (US)

( * ) Notice: Subject to any disclaimer, the term of this patent is extended or adjusted under 35 U.S.C. 154(b) by 341 days.

(21) Appl. No.: 10/392,167

(22) Filed: Mar. 19, 2003

(65) Prior Publication Data

US 2003/0179854 A1 Sep. 25, 2003

Related U.S. Application Data

(60) Provisional application No. 60/365,712, filed on Mar. 20, 2002.

(51) Int. Cl.
 *H01J 35/00* (2006.01)

(52) U.S. Cl. .................. 378/119; 378/136; 378/138
(58) Field of Classification Search .............. 378/119, 378/121, 122, 126, 136, 138, 207, 64, 65, 378/108, 109, 110, 111, 113
 See application file for complete search history.

(56) References Cited

U.S. PATENT DOCUMENTS

| 1,203,495 A | 10/1916 | Coolidge | 378/138 |
|---|---|---|---|
| 3,714,486 A | 1/1973 | McCrary | 378/122 |
| 5,090,043 A | 2/1992 | Parker | 378/122 |
| 5,153,900 A | 10/1992 | Nomikos | 378/65 |
| 5,165,093 A | 11/1992 | Miller | 378/138 |
| 5,651,045 A * | 7/1997 | Pouvesle et al. | 378/119 |
| 5,729,583 A | 3/1998 | Tang | 378/122 |
| 5,854,822 A | 12/1998 | Chornenky | 378/122 |
| 6,480,568 B1 * | 11/2002 | Dinsmore | 378/65 |
| 6,728,335 B1 * | 4/2004 | Thomson et al. | 378/65 |
| 2001/0016031 A1 | 8/2001 | Chornenky et al. | |

FOREIGN PATENT DOCUMENTS

| EP | 1 057 500 A1 | 6/2000 |
|---|---|---|
| WO | WO 01 18842 A1 | 3/2001 |

OTHER PUBLICATIONS

MICROSOFT® ENCARTA® ENCYCLOPEDIA 2001, "X Ray.", ©1993–2000 Microsoft Corporation.
Wolbarst, "Physics of Radiology," © 1993, pp. 82–83, Appleton & Lange, Norwalk, CT.
Coogan, JJ et al., "Production of High–Energy photons from Flash X–Ray Sources Powered by Stacked by Stacked Blumlein Generators".
"Review of Scientific Instruments", vol. 61, No. 5, May 1, 1990 NY pp. 1448–1456.

* cited by examiner

*Primary Examiner*—Edward J. Glick
*Assistant Examiner*—Courtney Thomas
(74) *Attorney, Agent, or Firm*—Craig Gregersen

(57) ABSTRACT

The present invention provides apparatus and method for providing a stabilized x-ray output from a field emission x-ray apparatus by monitoring the operating current and adjusting the gap between the anode and cathode to stabilize the output.

45 Claims, 7 Drawing Sheets

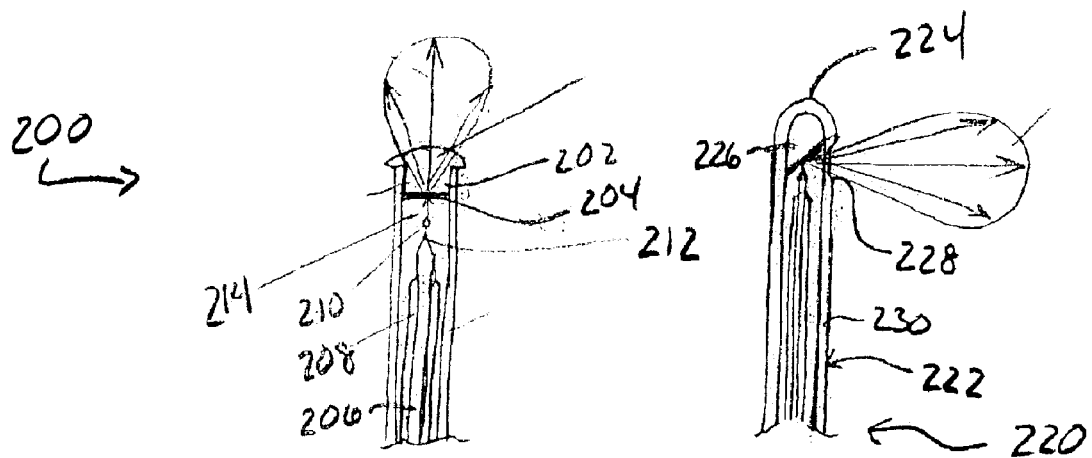
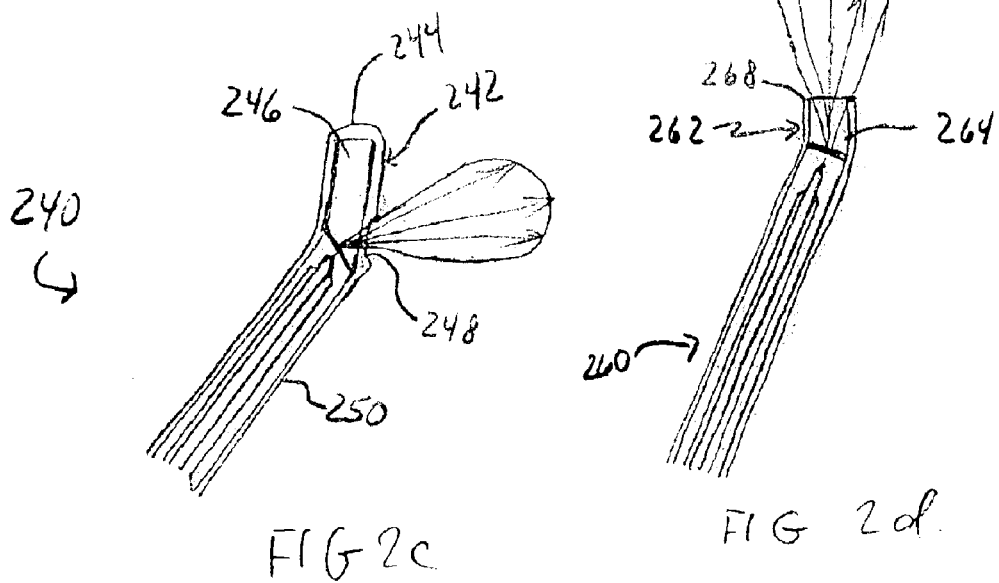

X-RAY APPARATUS WITH FIELD EMISSION CURRENT STABILIZATION AND METHOD OF PROVIDING X-RAY RADIATION THERAPY

The present application claims priority from U.S. Provisional Patent Application Ser. No. 60/365,712, entitled "X-ray apparatus for radiation therapy" and filed on Mar. 20, 2002.

The present invention relates generally to apparatus and method for providing x-ray radiation therapy and specifically to apparatus and method for providing x-ray radiation therapy with real-time stabilization of the operating current, and thus the dosage rate.

BACKGROUND OF THE INVENTION

The use of x-ray radiation for medical and non-medical applications is well known. In the medical arena, x-ray radiation therapy is a commonly used and accepted practice in the treatment of disease, including but not limited to, for example, tumors, certain skin diseases, and/or benign conditions. Historically, treatment first utilized external x-ray sources that supplied x-ray radiation to the target site. Where the target site was internal, such as a tumor, the applied x-ray radiation had to traverse the skin and other soft tissue and perhaps bone on its way to the target site, resulting in damage and burn to those tissues. Among other reasons, this disadvantage of x-ray therapy using external x-ray sources caused innovators to seek devices and methods to generate x-rays internally.

Generally speaking, there are two basic types of x-ray equipment in use today. One type relies upon heating an electron source to generate thermionically a beam of electrons that are then directed across a vacuum gap to a target material such as gold or tungsten or other high atomic number material. X-rays are generated upon the beam striking the target. In the second type, known as a field emission emitter, an electric field pulls electrons from a cathode across a vacuum gap toward an anode to strike a target material and generate the x-ray radiation. In both types, the generated electron beam is directed through a high vacuum to avoid electric breakdown and dissipation of the electron beam—and a subsequent reduction in the beam intensity—by atoms in the gap.

X-ray emitters for medical and non-medical applications take many forms. For example, one known type of emitter uses an x-ray source for intracavitary irradiation. The source comprises a housing, an elongated tubular probe, a target assembly, and an inflatable balloon. The housing encloses a thermionic electron gun and includes elements for directing the electron beam, generated in the housing, into the tubular probe. The tubular probe extends along a central axis from the housing about the beam path. The target assembly extends along the central axis and is coupled to the end of the probe distal from the housing. The target assembly includes a target element positioned in the beam path, and adapted to emit x-rays in response to the impinging electron beam. The balloon is affixed to the distal end of the probe and is inflatable so that when that probe end is inserted into a body cavity, the balloon may be inflated to stretch the cavity to a known shape.

The previously described apparatus has several drawbacks. First, the x-ray system has an inherent instability of its electron beam in the presence of a magnetic field. Because the thermionically generated electron beam must traverse the length of the probe between the electron gun and the target assembly, stray external magnetic fields can cause the beam to be deflected away from the target causing the generated x-ray flux to vary and complicating the calculation of the dose actually received by the patient. To address this drawback, the system requires an additional system for controlling the beam direction. Another drawback is that the apparatus includes an electron gun, which significantly adds both complexity and cost. Still another deficiency in this system is that the inflated balloon does not fix the position of the x-ray source relative to the patient's body and thus it requires an additional system for ensuring that the x-ray emitter is in the right position against the tissue to be irradiated.

Another x-ray device uses an X-ray needle for interstitial radiation treatment, This device includes an elongated X-ray tube coupled to an electron gun at one end of the tube, and a converter element converting the energy of electrons into the X-ray energy, disposed at the other end of the tube. The x-ray source comprises a solenoid coil wound around the tube for providing a magnetic field that confines the emitted electrons within a narrow beam. An elongated outer casing encloses the tube and coil. The x-ray source also includes a cooling system for removal of the heat generated by the converter and the magnetic coil. The drawbacks of the disclosed X-ray source are its relative complexity, large size and lack of adequate means for delivery of an optimal distribution of radiation dose across the predetermined volume of the target tissue.

Another known x-ray device utilizes a miniature X-ray tube with a direct current power supply and a field emission cathode. The tube has a needle cathode along its axis and an exit window at the end of the tube behind the cathode. The tube generates x-ray radiation along the axis of the device. It is not adapted for and cannot be used for treatment of tumors inside the body. Another drawback of the x-ray tube is an absence of the ability to control the operating current and voltage independently. This particular disadvantage inhibits manufacturing reproducibility.

In using x-rays for medical therapy it is important that the proper dose rate be applied. The dose depends upon the energy of the x-rays and the intensity of the x-ray beam. In field emission devices, increasing the voltage of the electric field increases the energy of the x-rays while increasing the current increases the intensity of the beam. Higher energy x-rays penetrate to greater depths in body tissue, so voltage control is important in controlling the energy to avoid damaging healthy tissue needlessly due to an undesired depth of penetration of the x-rays. The beam flux is also dependent upon the gap between the anode and the cathode. Increasing the gap decreases the beam flux and vice versa.

An undesirable feature of known field x-ray emitter devices is the inability to closely control the dose rate. One reason for this lack of control is that the generation of the electron beam from the cathode can be sporadic. That is, due to uncontrollable changes in the condition of the electron emitting surface of the cathode, field emitters are known for instability of their current, which can vary by a factor of 2. Because of the inconsistency in the current and thus the x-ray beam flux, the dose applied during any particular therapy session may not be well known, which leads to inconsistent treatment and results. The only sure way to know that a particular medical problem has been adequately addressed is to apply radiation at a presupposed rate that increases the likelihood of damage to healthy tissue.

There is a need for an apparatus and method that enables an operator of an x-ray apparatus to control the energy and intensity of an emitted x-ray beam by independently controlling the voltage and operating current, respectively. It would be desirable to have such an apparatus and method for use in standard operating rooms, which cannot currently be used where irradiation is supplied by widely used naturally occurring radioactive isotopes such as iridium 192 because of a lack of protection from the highly penetrating radiation produced by such sources. It would also be desirable to have an x-ray device that is not sensitive to the external magnetic field in the manner of x-ray sources using an electron gun. Additionally, it would be desirable for such an apparatus and method to provide a low cost source of ionizing radiation for radiation brachytherapy of brain, breast, prostate and other tumors or for radiation brachytherapy of non-tumor related medical problems such as macular degeneration in the eye.

BRIEF DESCRIPTION OF THE INVENTION

The present invention provides an apparatus and method for radiation therapy that enables the operator to exercise independent control of the voltage and operating current, thus providing the operator with the ability to stabilize the applied radiation dose supplied to the target site. An apparatus in accord with the present invention will have a field emission cathode that produces an electron beam in response to an applied operating current and an anode having a target material that generates x-rays when struck by the electron beam. The cathode and anode are separated by a gap changeable in size in response to the x-ray output of the device to maintain the dose at the desired level.

A method in accord with the present invention will involve steps of identifying a target site for radiation therapy; disposing a field emission x-ray apparatus having a cathode and an anode separated by a gap in proximity to the target site; monitoring the operating current of the x-ray apparatus; and adjusting the gap to maintain the desired operating current. Adjusting the gap enables the operator to control the operating current, thereby enabling compensation for possible instabilities in the field emission of electrons, including but not limited to instabilities caused by the state of the cathode emission surface, drift of operating parameters with time, and temperature.

In an embodiment of the present invention, an x-ray apparatus may have a vacuum housing and a probe attached thereto. The probe may have an elongated, tubular or needle-like configuration. The distal end of the probe may have a heavy-metal anode and a field emission cathode separated by a vacuum gap, the anode and cathode being provided for production of x-rays when an operating voltage is applied between them. Independent control of the operating current is provided to the operator by the inclusion of an adjustment mechanism for adjusting the gap size. In an embodiment of the invention, the adjustment mechanism may take the form of a linear translator.

For delivery of a predetermined radiation dose, the distal end of the probe is introduced into the body in proximity of the previously identified target or treatment site and the operating voltage is applied over a predetermined period of time. For optimal distribution of radiation along the treatment area a pullback mechanism may be provided that allows the operator to step-wise position and, if desired, rotate the probe during a radiation therapy procedure.

The cathode is adapted to emit electrons when an operating voltage is applied between the electrodes. As the electrons, emitted by the cathode, impinge on the anode, the x-rays are radiated in a predetermined spatial pattern. The irradiation pattern may vary for different implementation of the device. The depth of penetration of x-ray radiation in tissue is defined by the operating voltage and is predetermined for the procedure.

The present invention, as well as its various features and advantages, will become evident to those skilled in the art when the following description of the invention is read in conjunction with the accompanying drawings as briefly described below and the appended claims.

BRIEF DESCRIPTION OF THE DRAWINGS

FIGS. 2a–2d illustrate different alternate embodiments of the distal end of a probe of an x-ray apparatus in accord with the present invention.

DETAILED DESCRIPTION OF THE INVENTION

Figure 1:
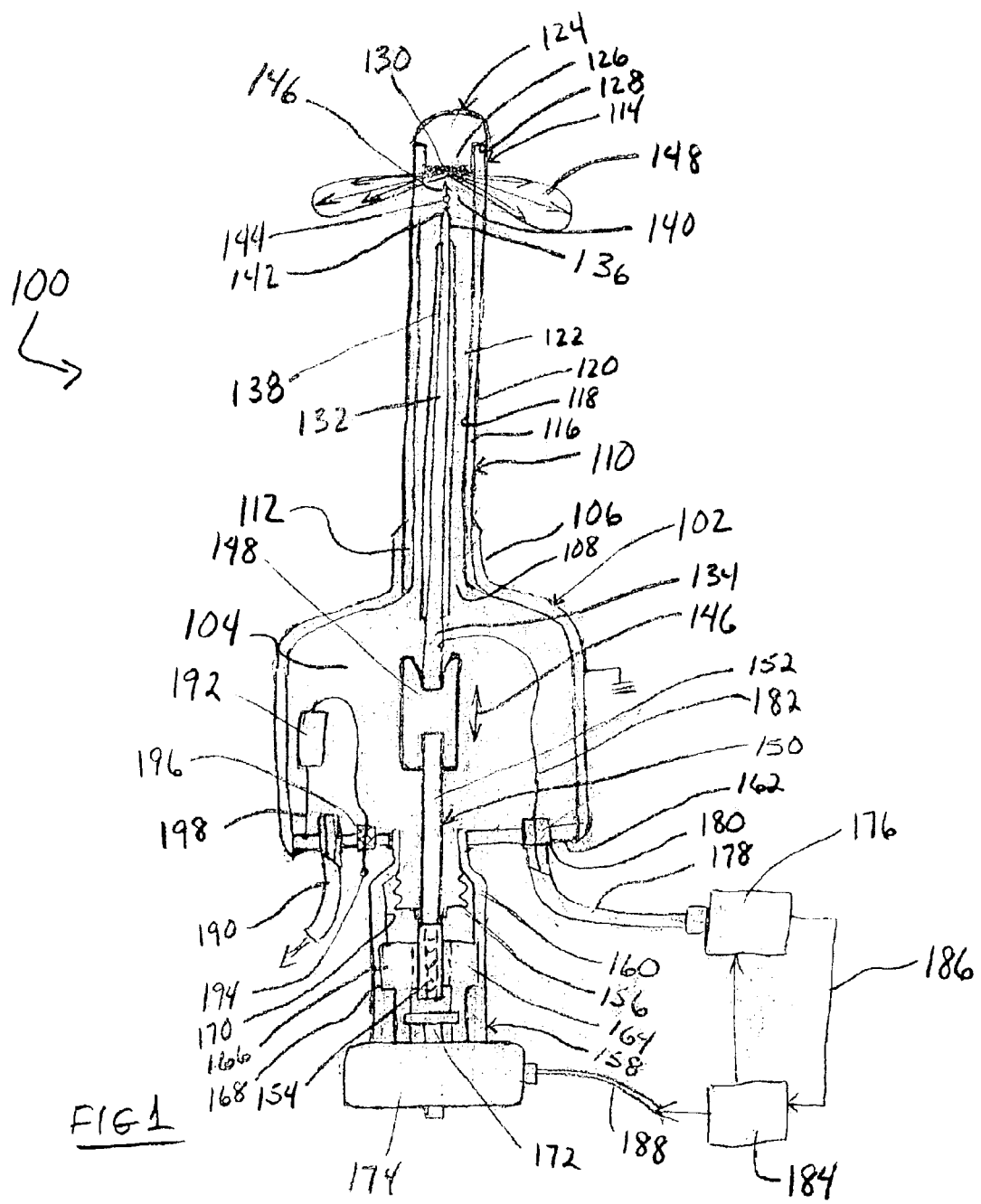
FIG. 1 illustrates an embodiment of the present invention in a partial cross sectional, partial schematic plan view.

An embodiment of an x-ray apparatus with gap size control 100 is shown in FIG. 1. Apparatus 100 includes a housing 102 that defines a vacuum chamber 104. Housing 102 can take substantially any desired form and as shown has a substantially cylindrical configuration. Housing 102 may include a collar 106 that may, if desired and as shown, be integral with the housing 102. Collar 106 forms an opening 108 into the housing 102 that is configured to receive a probe 110 having proximal and distal ends 112 and 114, respectively. Collar 106 receives proximal end 112 in a sealing engagement to preserve the vacuum within housing 102. While a protruding collar 106 is illustrated in the Figure, other known forms of sealing engagements and configurations therefor can be used with equal facility in the present invention so long as a vacuum can be maintained.

Probe 110 may have an elongate, tubular or needle-like configuration as shown in the Figure. It will be understood that while the embodiments of a probe used in association with the present invention shown herein will be described as being tubular or needle-like, that such descriptions are exemplary and that other shapes, if useful for a particular procedure, could also be used with the present invention. Thus, probe 110 includes an outer wall structure 116, here a cylindrical wall 116 having inner and outer surfaces 118 and 120, respectively, that defines a hollow interior 122 that communicates with vacuum chamber 104, and is thus also maintained as a vacuum, through its open proximal end 112. The other open, distal end 114 is sealingly enclosed by an anode electrode 124, which forms an end cap for the probe 110. Anode 124 includes an inwardly projecting mating portion 126 that is received within the probe 110 and a shoulder 128 that engages the end of the probe 110. Anode 124 can be sealingly attached to the probe 110 in any known manner, such as by brazing. In one embodiment of the present invention, anode 124 may be made of aluminum and may have a thin layer (0.25–0.5 microns) of gold, tungsten, or other known heavy metal, 130 deposited onto the anode surface A field emission cathode electrode 132 is disposed substantially within probe interior 122. Cathode 132 has proximal and distal ends 134 and 136. The cathode 132 is disposed substantially centrally within the probe 110 along its longitudinal axis, thus avoiding contact with the probe wall 116. Cathode 132 is preferably clad in an insulating layer 138 to prevent a high voltage electric breakdown between the cathode 126 and the probe 110, which is connected to the anode 124, during operation of the apparatus 100. Insulating layer 132 is preferably made from a high dielectric strength material.

Cathode 132 is spaced apart from anode 124 by a gap 140. When an operating voltage is applied across the gap 140 between the cathode 132 and the anode 124, the tip 142 of the cathode 132 emits electrons 144 (shown greatly exaggerated in size for purposes of illustration only) that travel across the gap 140 to the anode 124, as indicated by directional arrow 146. The radius of curvature of the sharp tip 142 is in a range of several tens of micrometers. As the electrons 144, emitted by the cathode 132, impinge on the anode 124, x-rays are radiated by the anode in a spatial pattern 148.

The depth of penetration of x-ray radiation emitted by anode 124 into tissue is defined by the applied operational voltage. During a radiation therapy procedure, a selected operating voltage is applied as previously discussed and the field emission cathode 132 starts emitting electrons 144, thus creating an operating current through the vacuum gap. The magnitude of this current depends in part on the size of the vacuum gap 140. As noted previously, known x-ray emitters are provided with gaps of fixed size, limiting the ability of the operator to control the radiation dose received by the patient. The present invention provides an operator greater control over the radiation dose by providing apparatus and method for adjusting the gap size, as will be described further below.

Thus, as seen in FIG. 1, the proximal end 134 of the cathode 132 is attached to an insulator 148, which, in turn, is secured to a movable shaft 150 at its distal end 152. The proximal end 154 of the movable shaft 150 has a fine thread and via a flexible bellow 156 is engaged with a translational stage 158. Translational stage 158 is secured to the vacuum housing 102 with a rigid tube 160 welded into the base plate 162 of vacuum housing 102.

Translational stage 158 comprises a threaded nut 164 that threadably receives the threaded proximal end 154 of the shaft 150. The outer perimeter 166 of nut 164 is rotationally received by an appropriately configured recess 168 in the inner surface 170 of the tube 160. Nut 164 is attached to a rotor 172 of a step motor 174. Rotation of the rotor 172 by motor 174 causes nut 164 to rotate, threading the proximal end 154 of the shaft 150 into or out of the nut 164 depending on the direction of rotation of the rotor. As the shaft 150 threads into or out of the nut 164, the tip 142 of the cathode 132 moves away from or towards the anode 124, changing the size of the gap 140 and thus regulating the operating current across the gap 140. Increasing the size of the gap decreases the operating current while decreasing the gap size increases the operating current.

The operating voltage for the apparatus 100 is provided by a high voltage DC source 176, which is connected the cathode 132 by an appropriate insulated connector 178. Connector 178 extends through base plate 162 through a high voltage feed-through 180. If desired, the electrical connector extending from feed-through 180 can be an uninsulated wire 182. DC source 176 should be configured to provide operating voltage in the range of about 10 to about 50 kV across the vacuum gap 140.

During an x-ray radiation therapy procedure, a desired radiation dose, which is a function of the dose rate and the time period during which the radiation is applied, will be determined and the appropriate voltage and current will be selected to provide the desired dose rate and time of irradiation using a controller 184. As noted, because the operating current can vary due to changes in the state of the cathode surface, the present invention affords the operator the opportunity to stabilize the operating current by adjusting the gap size 140. To that end, high voltage source 176 will include an appropriate current sensor (not shown in the Figure), which sends the value of the current via a feedback loop 186 to controller 184. In response to this current signal, controller 184 will send the appropriate signal through an appropriate connector 188 to motor 174. This signal will cause motor to rotate nut 164 in the appropriate direction to adjust the gap size and the operating current accordingly. In this manner, the current selected for the procedure by the operator can be stabilized stabilized with high precision by the feedback loop at any pre-selected operating value of the current. That is, by adjusting the gap size, the operating current is stabilized such that the desired dose rate is stabilized at the predetermined value for the predetermined irradiation time period (also monitored by the controller 184 using well-known timer electronics for doing so), thereby providing the desired total radiation dose for the particular radiation therapy.

Preservation of the vacuum within the apparatus 100 is important to its proper functioning. To that end, the probe 110 may be made of aluminum, so welding the probe to the anode 124 at the shoulder 128 to seal the probe/anode connection can be made relatively easily. In addition, base plate 162 may be joined to the vacuum housing 102 and tube 160 may be joined to the base plate 162 by vacuum tight welds. The ultra high vacuum ($10^{-7}$–$10^{-9}$ Torr) required for operation of field emission devices generally, is achieved by a vacuum pump, not shown in the figure, which evacuates the vacuum housing 102 via a pipe 190. When the outgassing and pumping out of the vacuum chamber 104 is complete, the pipe 190 is sealed and pinched off. A getter 192 maintains the high vacuum in the vacuum housing 102 after the apparatus 100 is separated from the vacuum pump. The getter 192 can be reactivated by a low voltage current delivered by connector 194 via a feed-through 196 in base plate 162. Getter 192 can be connected to the housing 102 by an appropriate connector 198 to complete a circuit. As is known in the art, getter 192 is provided to absorbs vacuum contaminants to preserve the vacuum at the desired level.

The present invention, in addition to providing dose control not found in the prior art, also can provide a variety of x-ray distribution patterns for different treatment situations. Examples of alternative embodiments of such and more detailed views of the distal end of the probe are shown in FIGS. 2a–2d. Each of the probes shown in the Figures are useful in the embodiment of the present invention illustrated in FIG. 1.

Referring to FIG. 2a, a probe distal end 200 includes an anode 202 made of beryllium vacuum sealed thereto. Anode 202 includes a thin layer 204 of heavy metal attached thereto by such known means as vapor deposition. A field emission cathode 206, clad in an insulating layer 208, emits electrons 210 (shown in greatly exaggerated detail) from the cathode tip 212 upon application of the operating current across the vacuum gap towards the anode 202. In this case, the beryllium anode 202 serves as the x-ray window and thus x-rays will be emitted in the forward direction in a substantially conical spatial pattern 216.

FIG. 2b illustrates a probe distal end 220 wherein the probe 222 has a closed end 224 with an aluminum anode 226 disposed therein. Anode 226 may also have a thin, heavy metal layer 204 deposited thereon. In this embodiment, the probe includes an x-ray window 228 in the cylindrical wall 230 of the probe 222. In this embodiment, x-rays will be emitted laterally to the longitudinal axis of the probe as indicated schematically by the spatial x-ray pattern 232. The x-ray window 228 is formed by reducing the thickness of the probe wall 230 in the desired area to facilitate the transmission of the x-rays from the probe into tissue.

FIG. 2c shows a probe 240 whose distal end 242 is angled relative to the axis of the probe, along which the cathode 206 generally lies. The distal end 242 of probe 240 has a closed end 244. A beryllium anode is disposed within the distal end of the probe. As in the embodiment shown in FIG. 2b, an x-ray window 248 is formed in the angled distal end 242 by thinning the wall 250, which made be made of aluminum, to facilitate transmission of the x-rays therethrough into the body tissue. As with the probe shown in FIG. 2c, x-rays will be emitted substantially at an angle to the axis of the probe.

FIG. 2d illustrates yet another embodiment of a probe 260. In this embodiment, a probe 260 includes an angled distal end portion 262. A beryllium anode 264 is sealingly received by the open end 266 of the angled distal end portion 262. The beryllium anode 264 will typically have a thin layer of heavy metal deposited thereon. In this embodiment, the beryllium anode 264 will serve as the x-ray window allowing transmission of the x-rays through from the probe into the tissue.

Figure 3:
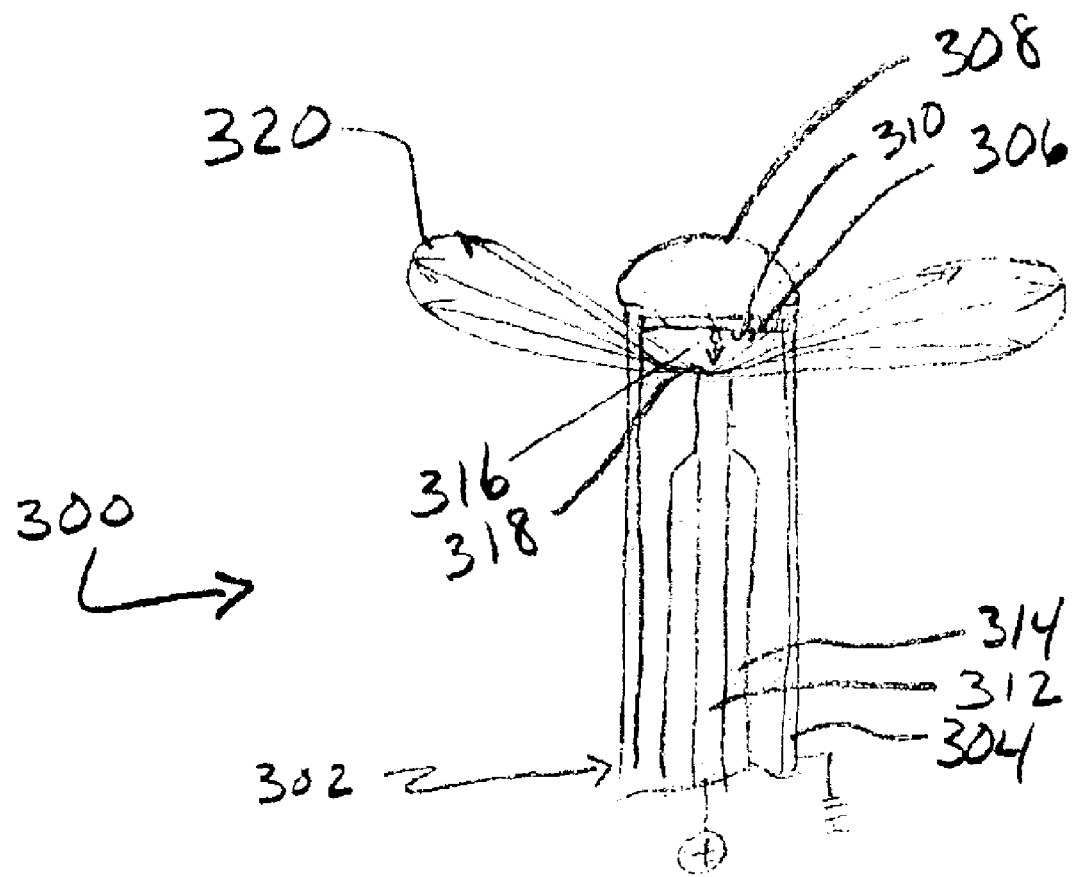
FIG. 3 depicts another alternate embodiment of the distal probe end of an x-ray apparatus in accord with the present invention.

FIG. 3 illustrates another embodiment of the distal end of a probe of a field emission x-ray apparatus in accord with the present invention. Thus, as shown, an alternative embodiment of a probe 300 includes a probe distal end 302 comprising a tube 304 having an open end 306 sealingly enclosed by an end cap 308 forming a field emission cathode. Cathode 308 includes a diamond film layer 310 (or a layer of a similar material that emits electrons) that serves as the electron emitter deposited thereon. An anode 312 is centrally disposed within tube 304 and during operation is maintained at a positive potential of about 10 to about 50 kV relative to the end cap cathode 306. Like the previously discussed cathodes of FIGS. 1–2d, anode 312 is clad in an insulating layer 314 to prevent high voltage discharges between the anode and the tube 304. In this embodiment, electrons are emitted by the layer 310, traverse a vacuum gap 316 and impinge upon the blunt end 318 of the anode, causing the emission of x-rays therefrom as indicated at 320. This reversal of the relative positions of the anode and cathode provides a higher hold-off voltage for the same diameter probe than the earlier described embodiments. In addition, any heat generated at the anode is dissipated by being carried by the anode rearwardly to the back plate of the housing (such as back plate 162 shown in FIG. 1) rather than being dissipated by the outer surface of the probe tube 304 into a patient's tissue, as may occur in the embodiments of FIGS. 1–2d. Stated otherwise, this embodiment allows a manufacturer to build a smaller, needle-type probe having a diameter of about 1 mm, which does not heat the probe and can be in direct contact with the patient body. This version of the emitter may be useful for treatment of prostate cancer among other illnesses.

Figure 4:
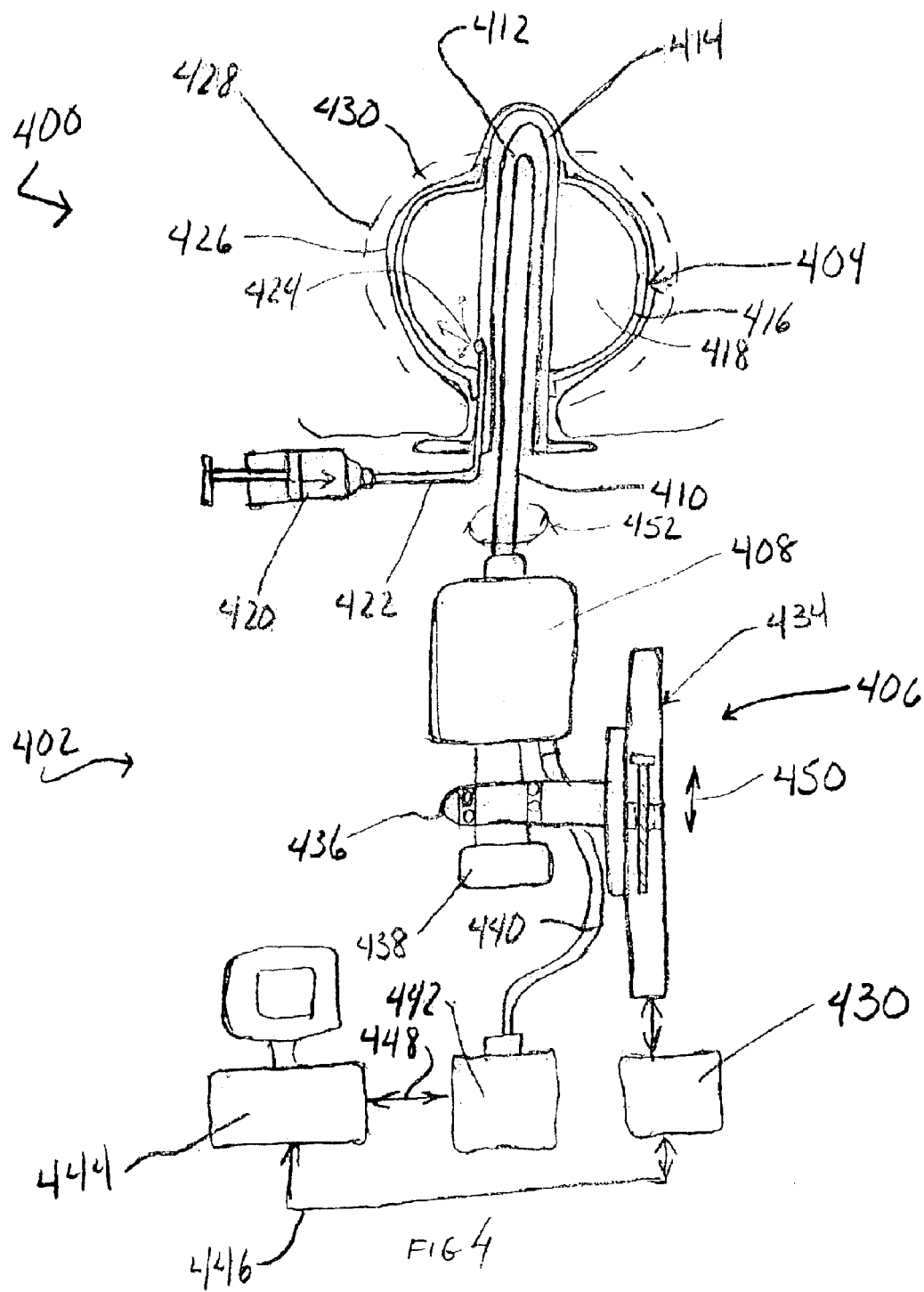
FIG. 4 schematically illustrates an x-ray apparatus in accord with the present invention and including a balloon and a pull-back mechanism.

FIG. 4 schematically illustrates an x-ray system 400 for radiation brachytherapy that may find use in irradiating marginal tissue after the removal of a tumor in a brain or breast. Irradiation of a tumor site following tumor excision is desirable because it helps ensure that any cancerous cells have been either excised or killed by the radiation, thus hopefully curing the patient. System 400 comprises an x-ray emitter apparatus 402, a balloon assembly 404, and a pullback system 406. Apparatus 404 includes a housing 408 and attached probe 410 in accord with previously described x-ray emitters. Probe 410 includes at its distal end 412 an anode/cathode x-ray emitter assembly that radiates x-rays radially in all directions. Balloon assembly 404 includes a hollow shaft 414 configured to slidingly receive the probe 410. An inflatable balloon 416 is attached to the exterior of the shaft 414. Balloon 416 includes an interior volume 418 that fluidly communicates with a syringe 420 via a hollow tube 422.

During an irradiation procedure, the balloon assembly 404 will be placed within a patient at a desired therapy site, such as a cavity formed within tissue by the removal of a tumor. Inflating the balloon assembly stretches the tissue surrounding the excised tumor and provides a more uniform surface for radiation therapy. Probe 410 can be placed inside the hollow shaft 404 of the balloon assembly 404 and the balloon 416 inflated by filling it with a fluid, such as saline, that is injected by the syringe 420, travels through the tube 422 and into the balloon interior volume 418 through a tube opening 424. Alternatively, the probe can be placed within the shaft after balloon inflation and moved therealong, irradiating the marginal tissue surrounding the inflated balloon 416. In the Figure, the cavity tissue surface lying adjacent to the balloon is designated by numeral 426, the reference surface outside the cavity tissue surface (usually 1 cm off the cavity surface 410) is designated by numeral 428, and the tissue to be irradiated, know as the marginal tissue, which lies between cavity tissue surface 426 and reference surface 428, is referenced by numeral 430.

To avoid excess radiation dosage delivery to some tissue and inadequate radiation dosage delivery to other tissue surrounding the balloon 416, pullback system 406 is provided to precisely control the movement of the probe 410 within the shaft 414. Pull back systems are known in the art and will be described generally here. System 406 comprises a controller 432 and a pullback mechanism 434. Mechanism 434 includes a clamp 436 that engages an appropriately configured connector arm 438.

System 400 further includes a high voltage connector 440 extending from the x-ray emitter high voltage source 442 to the housing as described in previous embodiments of the present invention, thus providing the high voltage power source 442 to the housing 408.

A computer or other microprocessor based device 444 may be used to control the motion of the probe 410 inside the shaft 414 and the dwelling times at each point along the shaft to deliver the dose to the reference surface 428 and the marginal tissue 430 exactly as prescribed for the particular patient and the particular procedure. Computer 444 will be connected to the pullback controller 432 with the appropriate connector 446 and to the high voltage power source 442 by an appropriate connector 448. In this manner, a single computer may easily control the entire procedure, controlling the operating current as previously described and advancing and retracting the probe within the shaft 414 as indicated by arrow 450. If desired, rotational motion may also be provided by such a system 406, as indicated by rotational arrow 452, or may be provided in lieu thereof by means known to the art. The details of the pullback system 406 are well-known and have been omitted from the Figures for clarity of illustration. Pullback systems can be purchased commercially, though they may need some modifications to engage an x-ray apparatus in accord with the present invention based upon the final configuration of the apparatus, such modifications being within the skill of those versed in the art.

Figure 5:
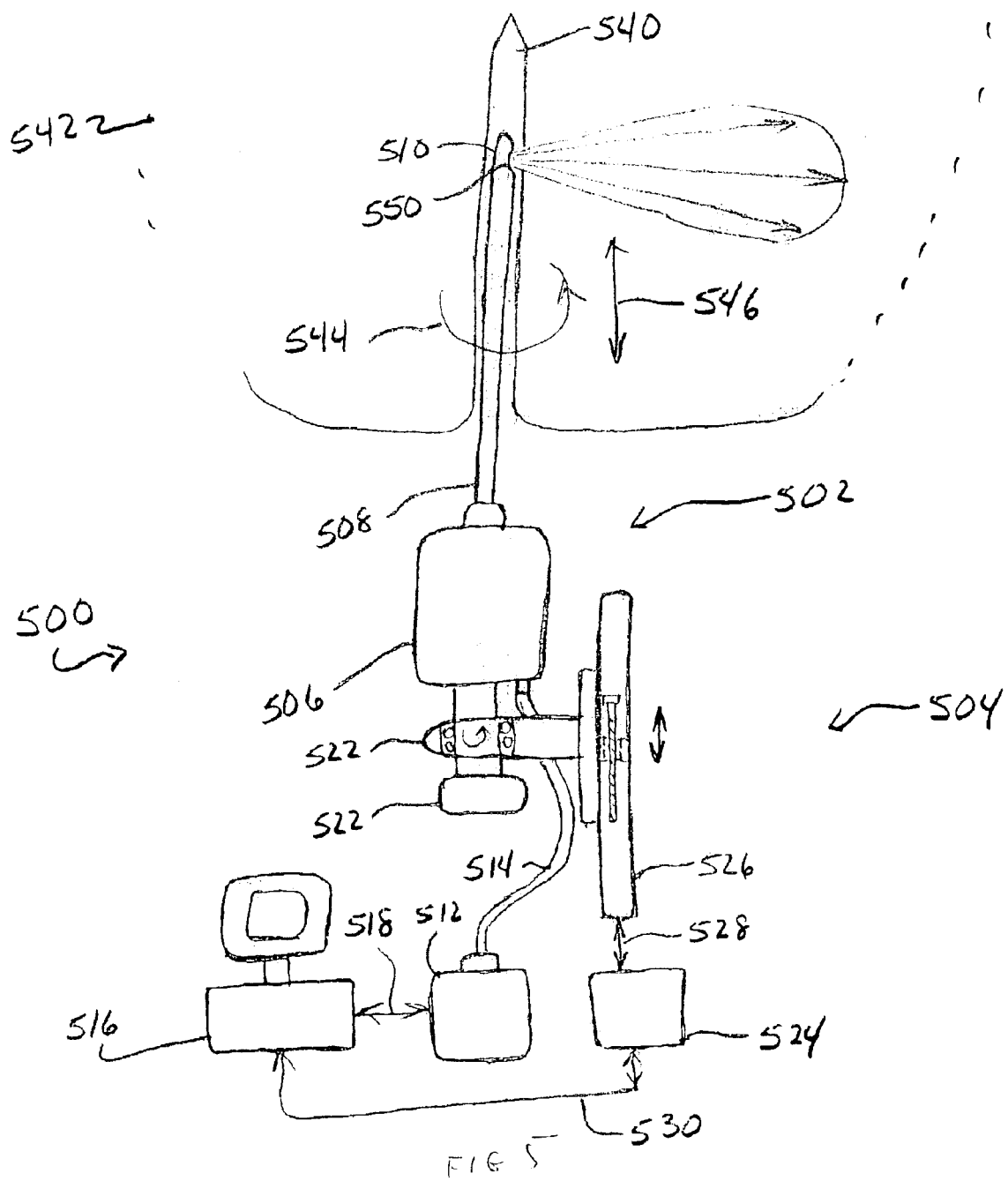
FIG. 5 schematically illustrates another embodiment of an x-ray apparatus in accord with the present invention.

FIG. 5 illustrates another embodiment of the present invention that can be used, among other uses, where no excision of the tumor is done and no balloon is used to stretch the cavity left after the excision. In this therapy situation, the irradiation is performed on a tumor in situ in the patient's body, and may be used, for example, for treatment of prostate cancer. Thus, FIG. 5 depicts an x-ray emitter system 500 comprising an x-ray apparatus 502 and a pullback mechanism 504. The apparatus 502 will be substantially similar to the previously described x-ray apparatus and the pullback system 504 will be substantially similar to the system 406 described with reference to FIG. 4, with any differences to be noted hereafter.

Thus x-ray apparatus 502 includes a housing 506 and a probe 508 having a distal end 510. X-ray apparatus 502 will be powered by a high voltage power source 512 connected thereto by an appropriate connector 514. Control of the high voltage power source 512 is accomplished with a computer 516 or other appropriate microprocessor device through an appropriate connector 518. Pullback mechanism 504 is attached by a clamp 520 or other attachment device known in the art to a connecting member 522 attached to the housing 506. Pullback system 504 comprises a controller 524 and a pullback mechanism 526 operably connected to each other by an appropriate connector 528. Operation of the pullback mechanism can also be controlled by computer 516 via an appropriate connector 528 to pullback controller 524.

In a therapy procedure using the x-ray system 500, an elongated cavity 540 will be made in a patient's body tissue 542 with a trocar or similar surgical instrument in the vicinity of the tumor or through the tumor itself. Subsequently, probe 508 will be introduced into the cavity 540. In this embodiment of the invention, an x-ray apparatus with one side irradiation pattern is utilized, similar to that shown in FIG. 2b or FIG. 2c. Movement of the probe to provide the desired, pre-selected radiation therapy will be accomplished by the pullback system 504. System 504 will be of the type that provides rotational motion to the probe 508, as indicated by the arrow 544 as well as translational motion as indicated by arrow 546. Thus, pull system 504 will be controlled by computer 516 to dispose the probe 508, and in particular, the probe distal end 510 with its x-ray window 550 in predetermined dwelling positions for predetermined periods of times in and around the tumor while also rotating the probe 508 to provide the desired radiation exposure pattern to the tumor and surrounding tissue. Probe pullback and rotation system 504 can thus provide an asymmetric radiation pattern, thereby avoiding over-irradiation of surrounding tissues, such as the patient's urethra and rectum when treating a prostate tumor, with vitally important functions. Protection of such tissues from an excessive radiation dose is important for long term success of such procedures; for example, excess irradiation of the urethra and rectum is known to be the major source of long term morbidity after an otherwise successful radiation treatment for prostate cancer.

Figure 6:
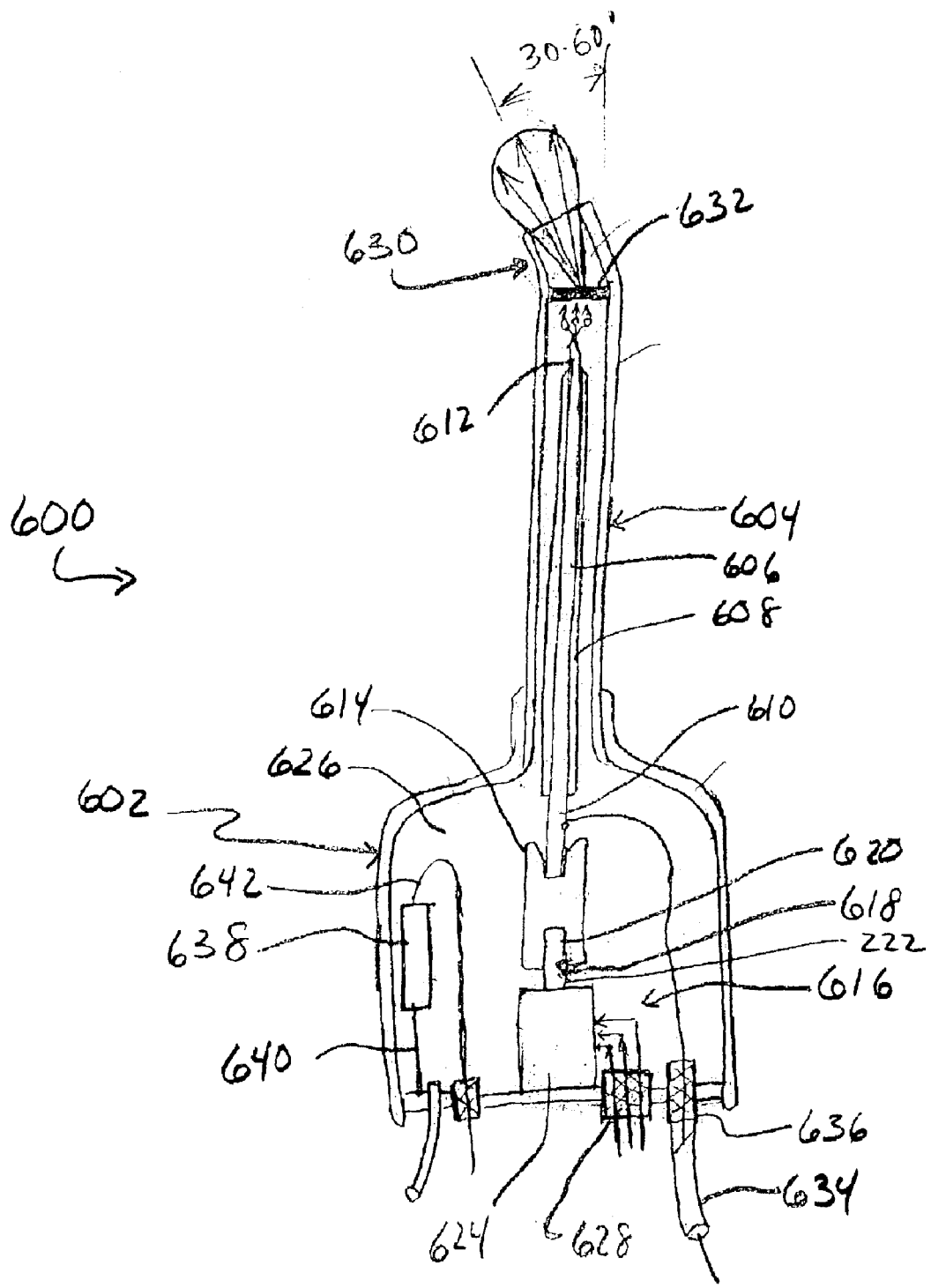
FIG. 6 schematically shows another embodiment of an x-ray apparatus in accord with the present invention wherein an inchworm linear motor is used to adjust the gap size.

FIG. 6 shows another embodiment of an x-ray apparatus 600 with an adjustable vacuum gap between the cathode and anode. Apparatus 600 is substantially similar to the embodiment 100 shown in FIG. 1. Thus, x-ray apparatus 600 includes a housing 602 and probe 604. A cathode 606 clad in an insulating layer 608 is disposed within the housing 602 and probe 604. Cathode 604 has proximal and distal ends 610 and 612. The proximal end 610 is connected to an insulator 614, which in turn is attached to a translation stage 616 to provide adjustment of the vacuum gap. Translation stage 616 comprises a shaft 618 that is attached at one or the distal end 620 to the insulator 614 and at the other or proximal end 622 to an inchworm linear motor 624. The inchworm linear motor 624 is a piezoelectric device generally used in micro-positioning applications due to its ability to make very small and accurate motions. One commercial source of such motor 624 is EXFO, which is located in Richardson, Tex. The inchworm linear motor 624 can be placed within the vacuum chamber 626 formed within the housing 602 and controlled via a three wire vacuum feed-through 628 by an external controller (not shown in the figure). The use of the inchworm linear motor 624 allows the overall size of the vacuum housing 602 to be reduced to about 6 to about 10 cm in length and about 2 to about 3 cm in diameter.

X-ray apparatus 600 probe distal end 630 is formed similarly to that embodiment shown in FIG. 2d wherein the distal end is angled relative to the longitudinal axis of the probe and cathode 606. In this embodiment, the emitted x-ray beam is angled about 30 to about 60 degrees with the axis of the probe 604. The distal end 630 mounts the anode 632 and the location of the angle with respect to the remainder of the probe body. Anode 632 is made from beryllium and includes a heavy metal deposit on it surface that functions as the x-ray emitter as previously described with respect to other embodiments.

Apparatus 600 is electrically connected to a high voltage power source (not shown) by an appropriate electrical connector 634 that extends through a feed-through 636. In addition, a getter 638 is provided; as with the embodiment shown in FIG. 1, getter 638 is electrically connected to an appropriate power source by electrical connectors 640 and 642 to provide reactivation.

Figure 7:
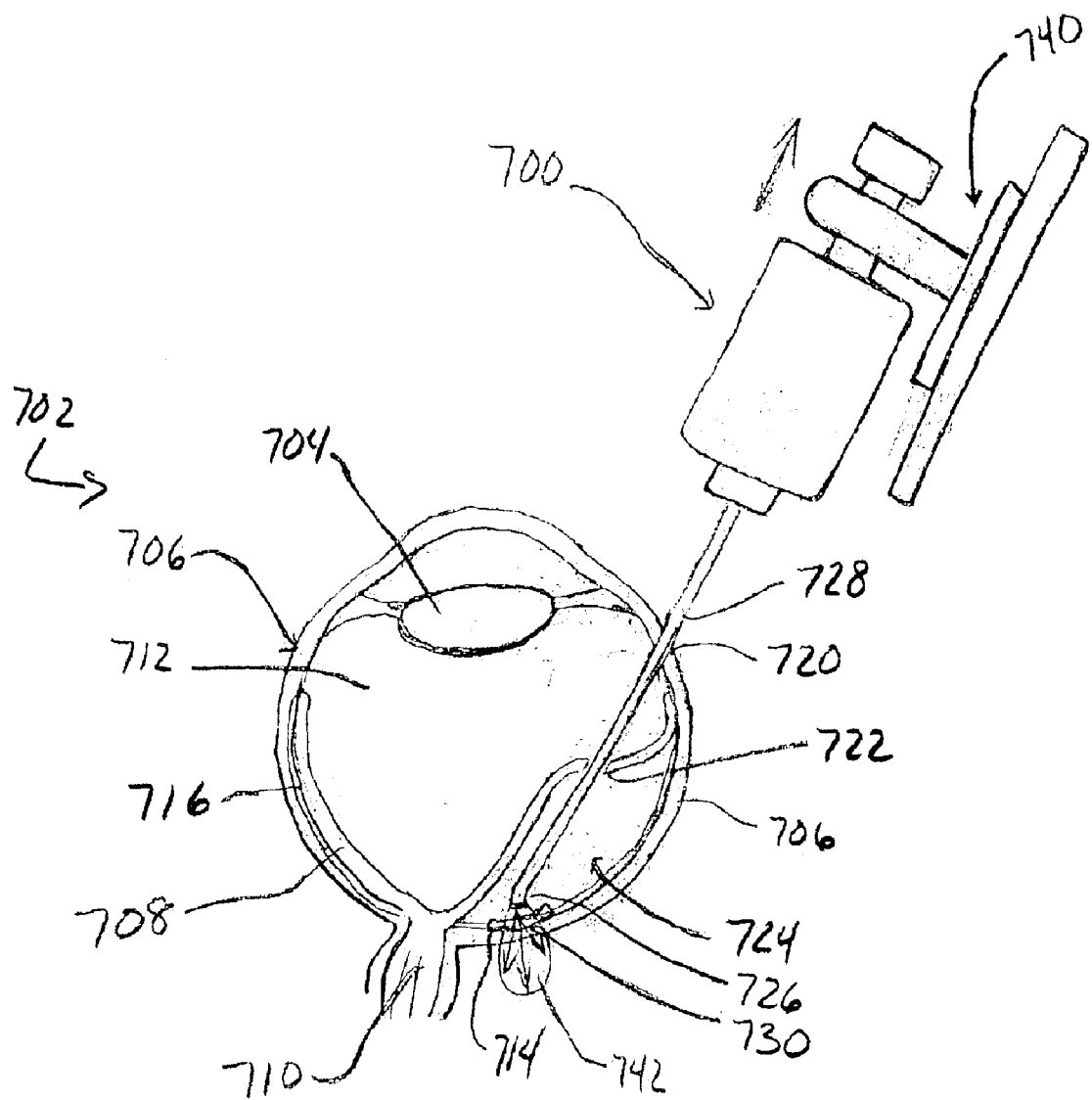
FIG. 7 illustrates an application of the present invention to the treatment of macular degeneration.

FIG. 7 depicts an application of an x-ray apparatus 700 in accord with the present invention to provide radiation therapy for the treatment of age-related macular degeneration, a leading cause of blindness.

A human eye 702 is shown in the Figure, with reference numerals 704, 706, 708, 710, and 712 designating the lens, sclera, retina, optic nerve, and vitreous cavity, respectively. The major detrimental syndrome of age related macular degeneration is the proliferation of blood capillaries 714, called choroidal neovascularization (CNV) behind the retina 708, or more precisely, within the space between the retina 708 and retinal pigment endothelium 716, which is a thin layer of cells too small to be seen in the Figure but whose location is indicated generally by reference numeral 716. This proliferation of new blood capillaries can lead to detachment of the retina and death of the light sensitive cells in the macular—the part of the retina responsible for central vision.

To treat age related macular degeneration, radiation treatment is given to the patient, with the objective of the therapy being to irradiate the newly proliferating capillaries with a sufficient radiation dose—in the range of about 15 to about 20 Grays—to kill them, after which the dead capillary cells are metabolized by the body. To provide such therapy, access is gained to the subretinal space 724 using known ophthalmological surgical techniques. Briefly described, the access procedure includes making a puncture 720 in sclera 706 to access first the vitreous cavity. The retina 708 is punctured next at 722 and may be followed by a gentle infusion of saline under the retina to elevate it away from the sclera 706 and create an inflated subretinal space 724 large enough to receive the distal end 726 of x-ray apparatus probe 728. For radiation treatment of the proliferating capillaries the distal end 726 is placed in the vicinity of macula 730 and a radiation dose is delivered using the apparatus 700 as previously described. For easy positioning of the x-ray probe 726 a positioning system 740 may be used. In a normal procedure, the positioning system 740 would be secured to a frame or support, which is not shown in the Figure for clarity of illustration. The system may include translational and rotational degrees of freedom for precise placement of the probe distal end 726 over the choroidal neovascularization 714 to be treated by radiation. As indicated in the Figure, x-rays 742 are emitted by the distal end of the probe to irradiate the CNV 714. Following delivery of the desired dose, the probe 728 will be withdrawn and the incision in the sclera is sutured.

The present invention has been described relative to several specific and various embodiments and procedures for use. Those skilled in the art will recognize that certain features described herein can be interchanged with other known devices. For example, but not limited thereto, adjustment of the vacuum gap has been accomplished by translational movement of the needle cathode (FIG. 1, for example) or the needle anode (FIG. 3, for example) by use of a step motor or inchworm linear motor. Any device, however, that can provide the desired translational movement with the requisite precision and size may be used with equal facility.

The present invention has been described in language more or less specific as to the apparatus and method features illustrated in the Figures. It is to be understood, however, that the present invention is not limited to the specific features described, since the apparatus and method herein disclosed comprise exemplary forms of putting the present invention into effect. For example, while the invention has been described relative to uses in the medical therapy field, it could find advantageous use whenever a field emission x-ray apparatus is used for any other purpose. The invention is, therefore, claimed in any of its forms or modifications within the proper scope of the appended claims appropriately interpreted in accordance with the doctrine of equivalency and other applicable judicial doctrines.

What is claimed is:

1. An apparatus for producing x-rays comprising:
    a housing;
    an elongate probe, said probe including:
        distal and proximal probe ends, with said proximal probe end being attached to and in vacuum communication with said housing; and
        an outer wall structure defining a hollow interior;
    an anode attached to said probe at said distal probe end;
    a field emission cathode having proximal and distal cathode ends, wherein:
        said distal cathode end is disposed within said probe hollow interior and spaced from said anode to create a gap therebetween; and
        said proximal cathode end is disposed within said housing; and
    a linear translator disposed in said housing and attached to said proximal cathode end, said linear translator being provided for moving said cathode toward and away from said anode during operation of said apparatus to adjust said gap and change the operating current.

2. The apparatus of claim 1 and further including:
    a high voltage power source electrically connected to said cathode, said power source including a sensor for sensing the operating current.

3. The apparatus of claim 1 wherein said linear translator includes:
    a shaft having proximal and distal ends, said distal end attached to said cathode and electrically insulated therefrom and said proximal end being threaded;
    a threaded nut receiving said threaded proximal shaft end; and
    a motor for rotationally driving said threaded nut.

4. The apparatus of claim 1 wherein said linear translator comprises:
    a shaft having proximal and distal ends, said distal end attached to said cathode and electrically insulated therefrom; and
    an inchworm linear motor engaged with said shaft.

5. The apparatus of claim 1 wherein said probe has a longitudinal axis and said distal end is angled relative to said longitudinal axis.

6. The apparatus of claim 1 wherein said cathode is clad with an insulating layer to electrically insulate it from said probe.

7. The apparatus of claim 1 and further including:
    a high voltage power source, said power source including a sensor for sensing the operating current and deviations from a predetermined operating current value; and
    wherein said linear translator includes:
        a shaft having proximal and distal ends, said distal end attached to said cathode and electrically insulated therefrom and said proximal end being threaded;
        a threaded nut receiving said threaded proximal shaft end; and
        a motor for rotationally driving said threaded nut
        wherein said motor drives said threaded nut to advance and retract said cathode and adjusts the size of the gap in response to a monitored deviation from the predetermined operating current to stabilize the x-ray output from the x-ray apparatus at a predetermined dose rate.

8. The apparatus of claim 1 and further including:
    a high voltage power source said power source including a sensor for sensing the operating current and deviations from a predetermined operating current value; and
    wherein said linear translator includes:
        a shaft having proximal and distal ends, said distal end attached to said cathode and electrically insulated therefrom; and
        an inchworm linear motor engaged with said shaft;
        wherein said inchworm linear motor advances and retracts said cathode and adjusts the size of the gap in response to a monitored deviation from the predetermined operating current to stabilize the x-ray output from the x-ray apparatus at a predetermined desired dose.

9. The apparatus of claim 1 and further including a pullback mechanism for advancing and retracting said probe relative to a target according to a predetermined therapy regimen.

10. The apparatus of claim 9 wherein said pullback mechanism rotates said probe according to a predetermined therapy regimen.

11. The apparatus of claim 1 and further including a mechanism for rotating said probe according to a predetermined therapy regimen.

12. The apparatus of claim 1 wherein said cathode is electrically insulated from said probe.

13. The apparatus of claim 1 and further including insulation disposed between said cathode and said probe.

14. An apparatus for providing x-ray radiation therapy comprising:
a housing;
an elongate probe, said probe including:
distal and proximal probe ends, with said proximal end being attached to and in vacuum communication with said housing; and
an outer wall structure defining a hollow interior;
an cathode attached to said probe at said distal probe end;
a anode having proximal and distal anode ends, wherein:
said distal anode end is disposed within said probe and spaced from said cathode to create a gap therebetween; and
said proximal anode end is disposed within said housing; and
a linear translator disposed in said housing and attached to said proximal anode end and being provided for moving said anode toward and away from said cathode during operation of said apparatus to adjust said gap and change the operating current.

15. The apparatus of claim 14 and further including:
a high voltage power source electrically connected to said anode, said power source including a sensor for sensing the operating current.

16. The apparatus of claim 14 wherein said linear translator includes:
a shaft having proximal and distal ends, said distal end attached to said proximal anode end and electrically insulated therefrom and said proximal shaft end being threaded;
a threaded nut receiving said threaded proximal shaft end; and
a motor rotationally driving said threaded nut.

17. The apparatus of claim 14 wherein said linear translator comprises:
a shaft having proximal and distal ends, said distal end attached to said anode and electrically insulated therefrom; and
an inchworm linear motor engaged with said shaft.

18. The apparatus of claim 14 wherein said anode is clad with an insulating layer to electrically insulate it from said probe.

19. The apparatus of claim 14 further including:
a high voltage power source said power source including a sensor for sensing the operating current; and
wherein said linear translator includes:
a shaft having proximal and distal ends, said distal end attached to said anode and electrically insulated therefrom and said proximal end being threaded;
a threaded nut receiving said threaded proximal shaft end; and
a motor rotationally driving said threaded nut
wherein said motor drives said threaded nut to advance and retract said anode and adjust the size of the gap in response to the monitored operating current to stabilize the x-ray output from the x-ray apparatus at a desired dose.

20. The apparatus of claim 14 and further including:
a high voltage power sources, said power source including a sensor for sensing the operating current and deviations from a predetermined operating current value; and
wherein said linear translator includes:
a shaft having proximal and distal ends, said distal end attached to said anode and electrically insulated therefrom; and
an inchworm linear motor engaged with said proximal shaft end,
wherein said inchworm linear motor advances and retracts said anode and adjusts the size of the gap in response to a monitored deviation from the predetermined operating current to stabilize the x-ray output from the x-ray apparatus at a predetermined dose rate.

21. The apparatus of claim 14 and further including a pullback mechanism for advancing and retracting said probe relative to a target according to a predetermined therapy regimen.

22. The apparatus of claim 21 wherein said pullback mechanism rotates said probe according to a predetermined therapy regimen.

23. The apparatus of claim 14 and further including a mechanism for rotating said probe according to a predetermined therapy regimen.

24. The apparatus of claim 14 wherein said anode is electrically insulated from said probe.

25. The apparatus of claim 14 and further including insulation disposed between said anode and said probe.

26. A method for providing radiation therapy to a patient comprising:
identifying a target for radiation therapy;
providing an x-ray apparatus including an anode and cathode separated by a gap for generating an x-ray emission;
disposing the x-ray apparatus in proximity to the target;
irradiating the target with x-rays produced by the x-ray apparatus;
monitoring the operating current of the x-ray apparatus to sense deviations from a predetermined operating current value; and
adjusting the gap between the anode and the cathode in response to a deviation of the operating current from its predetermined value to stabilize the x-ray emission to provide an irradiation dose rate for the therapy.

27. A method for treating macular degeneration comprising:
identifying choroidal neovascularization in a patient's eye for receipt of x-ray therapy;
providing access to the subretinal space in the patient's eye;
providing an x-ray apparatus for emitting x-rays for x-ray therapy, the apparatus having an elongate probe with a distal end including an anode and a cathode separated by a gap;
irradiating the choroidal neovascularization with x-rays produced by the apparatus;
monitoring the operating current of the x-ray apparatus; and
adjusting the gap between the anode and the cathode in response to a deviation of the operating current from a predetermined value to stabilize the x-ray emission to provide a desired irradiation dose rate for the therapy.

28. A method for providing x-ray radiation therapy to a tumor, said method comprising:
identifying a target in a patient's body for receipt of x-ray therapy;
providing access to the target;

providing an x-ray apparatus for emitting x-rays for x-ray therapy, the apparatus having an elongate probe with a distal end including an anode and a cathode separated by a gap;

irradiating the target with x-rays produced by the apparatus;

monitoring the operating current of the x-ray apparatus; and adjusting the gap between the anode and the cathode in response to a deviation of the operating current from a predetermined value to stabilize the x-ray emission to provide a desired irradiation dose rate for the therapy.

29. The method of claim 28 including providing a pullback mechanism for attachment to the x-ray apparatus, the pullback mechanism advancing and retracting the probe relative to the target according to a predetermined therapy regimen.

30. The method of claim 28 including providing a pullback mechanism for attachment to the x-ray apparatus, the pullback mechanism rotating the probe relative to the target according to a predetermined therapy regimen.

31. The method of claim 30 where in the tumor is in a prostate gland.

32. The method of claim 28 including advancing and retracting the probe relative to the tumor.

33. The method of claim 32 wherein the tumor is a prostate gland tumor.

34. The method of claim 33 including rotating the probe relative to the tumor.

35. The method of claim 24 wherein the tumor is in a prostate gland or a breast or a brain.

36. The method of claim 28 including rotating the probe relative to the tumor.

37. The method of claim 36 wherein the tumor is in a prostate gland.

38. The method of claim 28 including excising the tumor and disposing the probe distal end in the cavity created by the excised tumor.

39. The method of claim 38 including:

disposing a balloon assembly including a hollow shaft and an inflatable balloon in the cavity created by the excised tumor;

inflating the balloon to stretch the tissue surrounding the excised tumor; and inserting the probe into the hollow shaft for radiation therapy.

40. The method of claim 39 wherein the tumor is in a breast or a brain.

41. A method for generating x-rays with operating current control comprising:

providing an anode and a field emission cathode separated by a gap;

applying an electric field between the anode and cathode to generate an electron beam therebetween;

monitoring the operating current to detect deviations from a preselected value; and adjusting the size of the gap to return the operating current to the preselected value upon the occurrence of a deviation.

42. A method for providing radiation therapy to a patient comprising:

identifying a target for radiation therapy;

providing an x-ray apparatus including an anode and cathode separated by a gap for generating an x-ray emission;

disposing the x-ray apparatus in proximity to the target;

irradiating the target with x-rays produced by the x-ray apparatus; and adjusting the gap between the anode and the cathode at least once to stabilize the x-ray emission to provide a preselected irradiation dose rate for the therapy.

43. The method of claim 42 wherein the target is a choroidal neovascularization in the patient's eye.

44. The method of claim 42 wherein the target is a tumor.

45. An apparatus for producing x-rays comprising:

a vacuum housing;

an elongate evacuated probe, said probe including:
  distal and proximal probe ends, with said proximal probe end being attached to and communicating with said vacuum housing; and
  an outer wall structure defining a hollow interior;

an anode attached to said probe at said probe distal end;

a field emission cathode having proximal and distal cathode ends and being insulated from said probe, wherein:
  said distal cathode end is disposed within said probe and spaced from said anode to create a gap therebetween; and
  said proximal cathode end is disposed within said vacuum housing; and a system for stabilization of the field emission current comprising:
  a high voltage generator including a current sensor for monitoring the field emission current of said apparatus and;
  a linear translator disposed within said housing, said linear translator attached to said proximal cathode end and being provided for moving said cathode toward and away from said anode to adjust said gap during operation in response to changes in the operating current sensed by said current sensor and to thereby substantially stabilize the operating current at a predetermined value during operation.

* * * * *